United States Patent [19]

Heckelsberg et al.

[11] 4,386,229

[45] May 31, 1983

[54] OLEFIN DIMERIZATION

[75] Inventors: Louis F. Heckelsberg; William T. Nelson; Sidney Schiff; Ernest A. Zuech, all of Bartlesville, Okla.

[73] Assignee: Phillips Petroleum Company, Bartlesville, Okla.

[21] Appl. No.: 307,452

[22] Filed: Oct. 1, 1981

Related U.S. Application Data

[63] Continuation-in-part of Ser. No. 132,560, Mar. 21, 1980, Pat. No. 4,319,064.

[51] Int. Cl.$^3$ ............................................... C07C 1/16
[52] U.S. Cl. .................................. 585/255; 585/329; 585/510; 585/525
[58] Field of Search ................ 585/255, 329, 510, 525

[56] References Cited

U.S. PATENT DOCUMENTS

| | | | |
|---|---|---|---|
| 2,412,595 | 12/1946 | Axe | 585/450 |
| 3,271,473 | 9/1966 | Engelbrecht et al. | 585/510 |
| 3,330,882 | 7/1967 | Albright | 585/329 |
| 3,382,291 | 5/1968 | Brennan | 585/521 |
| 3,393,251 | 7/1968 | Fenton | 585/510 |
| 3,676,520 | 7/1972 | Heckelsberg | 585/647 |
| 3,742,082 | 6/1973 | Brennan | 585/255 |
| 3,763,244 | 10/1973 | Shubkin | 585/18 |
| 3,769,363 | 10/1973 | Brennan | 585/255 |
| 3,780,128 | 12/1973 | Shubkin | 585/12 |
| 3,890,402 | 6/1975 | Stapp | 585/510 |
| 3,997,621 | 12/1976 | Brennan | 585/255 |
| 4,143,087 | 3/1979 | Bamforth et al. | 585/510 |
| 4,166,796 | 9/1979 | Reechuite | 252/48.6 |

FOREIGN PATENT DOCUMENTS 1497524  1/1978  United Kingdom .

*Primary Examiner*—Curtis R. Davis

[57] ABSTRACT

Internal olefins such as those obtained from a disproportionation of 1-olefins like 1-decene are dimerized over a promoted boron trifluoride catalyst to yield oils useful as lubricant basestock.

11 Claims, No Drawings

OLEFIN DIMERIZATION

This application is a continuation-in-part of Ser. No. 132,560, filed Mar. 21, 1980, now U.S. Pat No. 4,319,064.

This invention relates to the production of an oil from a specific olefin. In another aspect, this invention relates to the synthesis of an oil having a low pour point and being useful in lubrication. Still another aspect of this invention is a new dimerization reaction.

BACKGROUND OF THE INVENTION

Hydrocarbon conversions and particularly the reactions of olefins constitute a very important section of the organic chemistry. The 1-olefins can be polymerized to high polymers, they can be alkylated to high octane fuels and they can be oligomerized to oils.

Lubricating oils have been refined in recent years to match the increasing demands concerning their performance. Not only many additives have been developed for lubricating oils, but also entirely synthetic oils have been produced which exhibit special properties not found in oils produced from crude petroleum alone.

One of the key features in many chemical reactions is the desired purity of the end product. This feature is particularly difficult to achieve in hydrocarbon conversion reactions. The larger the hydrocarbon molecules are, the more difficult it becomes to perform a reaction with only one or two reaction products resulting therefrom. Particularly, producing a hydrocarbon oil with a well defined molecular weight and structure is a continuing goal in the petrochemical industry. Such pure oils can then be used as such or blended into other mixtures with reproducible and reliable properties.

Among the known hydrocarbon conversion reactions, dimerization is of particular interset here. Furthermore, the disproportionation (metathesis) reactions are important for this invention.

Olefin oligomerization and particularly dimerization reactions are well known in the art. These reactions start from 1-olefins, i.e. hydrocarbons having a double bond at the end of a hydrocarbon chain. The dimerization reaction is normally carried out by contacting the 1-olefin with a dimerization catalyst. One known procedure utilizes for instance 1-decene and subjects it to an oligomerization in which dimers, trimers, and tetramers are produced with respectively 20, 30 and 40 carbon atoms in the molecule. One problem in this process is that a significant portion of each of these oligomers is produced and that the products therefore have a fairly wide spread of molecular weight.

STATEMENT OF THE INVENTION

It is an object of this invention to provide a new process for dimerizing a hydrocarbon with good selectivity.

Another object of this invention is to provide a process for combining 4 olefin molecules with high selectivity into a desired oil compound. Yet another object of this invention is to provide a process for producing a hydrocarbon oil useful in lubrication from 1-olefins.

Other objects, advantages, details, features and embodiments of this invention will become apparent to those skilled in the art from the following detailed description of the invention and the appended claims.

In accordance with a first embodiment of this invention a new hydrocarbon is provided which can be characterized as tetra-n-alkylethylene having 28 to 44 carbon atoms per molecule with the proviso that the n-alkyl radicals have 4–13 carbon atoms. The new composition of matter can also be characterized by the structural formula

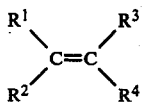

wherein $R^1$, $R^2$, $R^3$ and $R^4$ are n-alkyl radicals of 4 to 13 carbon atoms. These new substituted ethylenes are oils that prior to and particularly after hydrogenation are useful as lubricating oils. In addition these substituted ethylenes are valuable intermediates for the production of other organic chemicals.

The hydrogenated compounds are also believed to be novel composition and constitute another embodiment of this invention. These 1,1,2,2,-tetra-n-alkyl-ethanes having 28 to 44 carbon atoms per molecule can be characterized by the formula

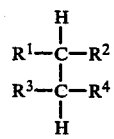

wherein the radicals $R^1$–$R^4$ have the meaning defined above. The new compositions are as such useful as lubricating oils or can be blended with other ingredients to form lubricating oils. The preferred tetra-substituted ethylenes and ethanes are those in which the n-alkyl radicals $R^1$–$R^4$ have 6–9 carbon atoms.

In accordance with a further embodiment of this invention it has been found that specific internal olefins can be converted into hydrocarbon oils with good selectivity to the desired oil by contacting these internal olefins with a promoted boron trifluoride catalyst under dimerization conditions. The present invention utilizes as the starting material for the dimerization process an internal olefin having the formula $$R\text{---}CH\text{=}CH\text{---}R' \qquad (1)$$

In this formula, R and R' can be the same or different and represent alkyl radicals having 4 to 12 carbon atoms.

Another embodiment of this invention resides in a process to produce a mixture containing a hydrocarbon oil useful in lubrication from a 1-olefin. This process comprises essentially the following three steps:

(a) contacting at least one 1-olefin having the formula $$R''\text{---}CH\text{=}CH_2 \qquad (2)$$

wherein R" has the same meaning as R and R' above, with a disproportionation catalyst under disproportionation conditions.

(b) The unreacted 1-olefins and the internal olefin of the formula (1) above are then separated.

(c) The internal olefin of the formula (1) above thus separated and being essentially free of unreacted 1-olefins is then contacted with a dimerization catalyst under dimerization conditions to form a mixture containing the desired hydrocarbon oil.

Ideally the process of this invention can be illustrated by the formulae:

Metathesis:

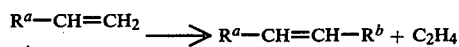

Dimerization:

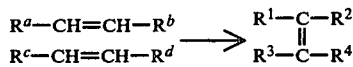

with two of the radicals $R^1$, $R^2$, $R^3$, $R^4$, selected from $R^a$, $R^b$, $R^c$, $R^d$, and the other two of the radicals $R^1$-$R^4$ selected from $-CH_2-R^a$, $-CH_2-R^b$, $-CH_2-R^c$, $-CH_2-R^d$. The number of carbon atoms in all four radicals $R^a$, $R^b$, $R^c$, $R^d$ together being equal to the number of carbon atoms in all radicals of $R^1$, $R^2$, $R^3$, and $R^4$ together minus 2.

Any U.S. patent referred to in this specification for further details consistent with this specification is insofar incorporated into this specification by reference.

Metathesis Step

In the disproportionation or metathesis step of the combined process of this invention alpha olefins can be used that have 6 to 14 carbon atoms. Examples of such olefins are hexene-1, heptene-1, octene-1, nonene-1, decene-1, undecene-1, and dodecene-1. The octene, nonene, and decene homologs are particularly preferred. The normal isomers of these olefins are preferred, although small concentrations of branched isomers can be present. Branched alpha olefins reduce the viscosity index of the oil produced and hence are less desirable components of the starting material.

The initial step of the combined process is the metathesis or disproportionation of alpha olefins to produce a larger internal olefin as follows:

where R and R' are alkyl radicals, preferably n-alkyl radicals, having 4 to 12 carbon atoms. The preferred olefin feedstock is one in which R and R' are the same. In this reaction it is very desirable to prevent or minimize isomerization of the double bond in the olefin product. If a small degree of isomerization in the metathesis should occur, it is contemplated that this will not shift the double bond by more than two carbon atoms. In other words, R' in the internal olefin may have one or two carbon atoms more (less) than R' of the starting 1-olefin, and correspondingly R in such an internal olefin will then have one or two carbon atoms less (more) than R of the starting 1-olefin, without leaving the scope of this invention.

Consequently the metathesis reaction is preferably effected at a mild temperature, and with a catalyst useful under mild disproportionation conditions, such as one comprising an oxide of rhenium. U.S. Pat. No. 3,676,520 discloses such a catalyst. The presently preferred disproportionation catalyst in $Re_2O_7$ on alumina.

The temperature for the metathesis reaction can be from about 0°–50° C.; preferably it will be between 20°–30° C.

The pressure for the metathesis reaction can be from about 0.01 to 2 atmospheres absolute ($1 \times 10^3$ to $2 \times 10^5$ Pa). For convenience atmospheric pressure is preferred. These relatively low pressures permit continuous or frequent removal of the ethylene produced in the reaction. Without its removal the internal olefin can be cleaved to regenerate the alpha olefins via the reverse metathesis reaction.

Olefin metathesis can be effected continuously or batchwise; for this process the batchwise mode is preferred. Using a catalyst as disclosed in the above identified patent, the weight ratio of alpha olefin to catalyst can range from 1:1 to 100:1. The preferred ratio is about 10:1 to 50:1. It is generally impractical to convert all the alpha olefins because of reaction rates. However, contact time between catalyst and olefin for batchwise reaction can range between about 1–1000 hours; preferably the contact time is 10–500 hours.

If continuous metathesis is to be effected, catalyst and conditions disclosed in U.S. Pat. Nos. 3,658,927 and 3,586,731 can be used. The former teaches catalysts supported on alumina and the latter teaches catalysts supported on silica. These catalysts are treated with alkaline materials that reduce or destroy catalyst acidity that causes double bond isomerization as described in detail in U.S. Pat. No. 3,586,731. Use of the lower temperatures cited in these patents will help to minimize the undesirable isomerization.

The metathesis catalyst is separated from the hydrocarbon product in a manner that is well known in the art. Such a separation is, for instance, described in the U.S. Pat. No. 3,558,518, col. 9. Other possibilities for separating the disproportionation catalyst from the hydrocarbons produced would be filtration or centrifugation where applicable.

Olefin Separation Step

Following alpha olefin metathesis, unreacted alpha olefins are separated from the internal olefin product of that reaction. Distillation provides a convenient way to make the separation and, unless the alpha olefins selected for the metathesis reaction contained too large a range of molecular weights, there will be a large break between the boiling point of the highest boiling alpha olefin and the lowest boiling internal olefin product.

This separation of the alpha olefins from the internal olefins for the preferred embodiment of this invention utilizing olefins with 8 to 10 carbon atoms is thus carried out by distillation in which the end point for alpha olefins at atmospheric pressure is not above about 175° C. and the initial boiling point of the internal olefin is not below about 235° C. The alpha olefin thus separated is preferably recycled to the metathesis step.

Dimerization Step

The separated product of the metathesis reaction (which is essentially free of alpha olefins) is converted by dimerization to compounds that are useful as lubricating oil basestock. The catalysts that can be used to effect dimerization, are halides of aluminum or boron, such as Friedel-Crafts catalysts, particularly promoted boron trifluoride catalysts. Other examples of catalysts include aluminum trichloride ($AlCl_3$), preferably employed in solution and promoted by a hydroxy compound, such as a small amount of water. The alcohol-promoted boron trifluoride catalysts are preferred. Preparation and use of such catalysts are disclosed in U.S. Pat. No. 3,780,128, Col. 2, line 48 to Col. 5, line 15. The oligomerization of less reactive internal olefins in the invention is carried out at preferably higher temperatures than those disclosed in this patent. Although temperatures in the range −10° to 150° C. can be used for dimerization, the preferred range is about 40°-80° C. The other details concerning the catalyst composition and concentration, method of effecting the reaction, time and pressure of reaction, removal of catalyst, and hydrogenation of the resulting hydrocarbon to produce a synthetic lubricant base stock from U.S. Pat. No. 3,780,128 is applicable to this step of the invention process also, and is herewith incorporated by reference.

The hydrocarbon oil produced as well as any unreacted internal olefin are then removed from the dimerization catalyst. This separation is done by conventional techniques such as those described in U.S. Pat. No. 3,763,244. Other methods to separate the hydrocarbons from the catalyst are filtering or centrifuging.

Recovery and Purification of the Oil Product

To obtain the desired physical properties in the synthetic lubricant it is frequently desirable to distill the mixture remaining after the dimerization step. The concentration of unreacted internal olefin is generally small but, after removal of the alcohol-promoted boron trifluoride catalyst, it can be removed by distillation and returned to the dimerization process.

In the preferred embodiment of this invention this distillation step is done by heating the hydrocarbon mixture to a temperature usually in the range of 350° C. to 400° C. The temperature is between the boiling point of the highest boiling internal olefin and the boiling point of the lowest boiling dimer of the internal olefins.

Product having unacceptably high molecular weight preferably is removed by vacuum distillation. The hydrocarbon oil in this process is removed as the distillate whereas the undesirably high molecular weight product is removed as the bottom product from a distillation column. The vacuum distillation is usually carried out under a pressure of 0.01 torr to 100 torr preferably 1-5 torr, and by heating the product to obtain a product that has a corrected boiling point less than about 525° C. The thus purified and evaporated oil is recondensed and recovered.

Prior to or after the vacuum distillation the oil produced is generally catalytically hydrogenated. This hydrogenation is done in a conventional procedure such as the one described in U.S. Pat. No. 2,270,303. Typical hydrogenation catalysts that can be used are Ni on alumina, cobalt molybdate on alumina, Pd, Pt, or Ru on alumina or carbon, but not acidic supports. The contacting of the oil produced with hydrogen and the hydrogenation catalyst is preferably carried out while the hydrocarbon oil is in the vapor phase as the distillate coming from the vacuum distillation for removing the high molecular weight product described above.

Without undue limitation, the following examples describe further preferred details of this invention.

EXAMPLE 1

Metathesis of five different alpha olefin compositions was made. All runs started with 1-octene and/or 1-decene which were contacted with 9 wt. % $Re_2O_7$ on alumina catalyst. The quantities of the ingredients as well as the reaction conditions are shown in the following table. Before each run the catalyst was activated by heating in flowing air at 450° C. for three hours, then flushed with nitrogen at that temperature for 20 minutes, and cooled. It was placed in an oven-dried oxygen-free flask which was then closed with a rubber serum closure. Measured quantities of alpha olefin were added to the flask and it was allowed to stand at ambient temperature (about 25° C.). During reaction the flask was vented via a hypodermic needle through the serum cap to permit ethylene produced in the metathesis reaction to escape. The product was separated from the catalyst by filtration. Table I summarizes the five runs, including the composition of the product as determined by gas-liquid chromatography (GLC) at the times indicated.

TABLE I

| | Run | | | | | | |
|---|---|---|---|---|---|---|---|
| | I | II | III* | IV* | V | VI | |
| Feed composition, moles | | | | | | | |
| 1-Octene | 2.6 | — | 3.0 | 0.51 | 0.50 | 1.0 | 0 | — |
| 1-Decene | 0 | — | 1.0 | 0.54 | 0.50 | 3.0 | 2.1 | — |
| Wt. catalyst, g | 44 | — | 50 | 32 | 50 | 50 | 44 | — |
| Reaction time, hr | 66 | 90 | 90 | 20 | 40 | 90 | 92 | 116 |
| Product analysis, wt. % | | | | | | | | |
| $C_7$ | — | — | tr | 0.4 | 0.1 | 0.3 | — | — |
| $C_8$ | 33.0 | 32.5 | 24.7 | 17.6 | 8.8 | 6.8 | — | — |
| $C_9$ | 0.3 | 0.9 | 0.5 | 0.2 | tr | tr | — | — |
| $C_{10}$ | 0.3 | 0.6 | 9.4 | 25.7 | 11.3 | 28.2 | 35.4 | 31.9 |
| $C_{11}$ | 1.8 | 2.0 | 1.3 | 0.4 | 0.8 | 0.4 | 0.8 | 0.8 |
| $C_{12}$ | — | 0.2 | 0.2 | 0.1 | 0.2 | 0.4 | 0.8 | 0.7 |
| $C_{13}$ | — | 0.2 | 1.0 | 0.5 | 1.3 | 1.2 | 1.8 | 1.8 |
| $C_{14}$ | 64.3 | 61.9 | 34.1 | 10.4 | 15.1 | 2.9 | 0.5 | 0.4 |
| $C_{15}$ | 0.3 | 0.2 | tr | 0.3 | 0.8 | 1.2 | 2.0 | 2.4 |
| $C_{16}$ | — | 1.6 | 24.7 | 27.9 | 40.3 | 22.7 | 0.6 | 0.4 |
| $C_{17}$ | — | — | tr | — | tr | 0.1 | 0.2 | 0.2 |
| $C_{18}$ | — | — | 4.1 | 16.5 | 21.3 | 35.7 | 57.4 | 61.0 |
| $C_{19}+$ | — | — | — | tr | tr | 0.1 | 0.5 | 0.4 |
| 1-Olefin conversion, % | 67.0 | 67.5 | 65.9 | 56.7 | 79.9 | 65.0 | 64.6 | 68.1 |

*Runs III and IV were made with a partial vacuum (~$10^4$ Pa) on the reaction flask to facilitate removal of ethylene. About 8 wt. % of $C_8+$ 30 was also lost to the vacuum during the reaction period.

The products anticipated from metathesis of these alpha olefins were produced with good selectivity at these conditions, namely, $C_{14}$ from 1-octene, $C_{18}$ from 1-decene, and $C_{14}$, $C_{16}$, and $C_{18}$ from mixtures of 1-octene and 1-decene. The concentration of olefins having odd carbon numbers, which result from undesirable double bond isomerization, is low.

In runs I and VI the reaction mixture was analyzed at two different times. The results show that the reaction is not fast, but maintains its selectivity. Runs III and IV were made at reduced pressure; run IV showed the highest alpha olefin conversion of all runs, at the relatively short reaction time of 40 hours.

Reaction mixtures from metathesis of 1-octene and/or 1-decene were subjected to distillation to separate the heavier metathesis product from the reactants. Table II summarizes the composition of the mixture after the $C_{10}$-fraction had been removed.

TABLE II

| | Run | | | | |
|---|---|---|---|---|---|
| | VII | VIII | IX | X | XI |
| Metathesis feed, mole % | | | | | |
| 1-Octene | 100 | 75 | 50 | 25 | 0 |
| 1-Decene | 0 | 25 | 50 | 75 | 100 |
| $C_{11}+$ fraction, wt. % | | | | | |
| $C_{10}$ | | | 0.3 | | |
| $C_{11}$ | | 1.2 | 0.6 | | |

TABLE II-continued

| | Run | | | | |
|---|---|---|---|---|---|
| | VII | VIII | IX | X | XI |
| $C_{12}$ | 0.4 | | 0.4 | 0.6 | |
| $C_{13}$ | 1.6 | 0.8 | 1.7 | 1.9 | |
| $C_{14}$ | 94.8 | 43.7 | 18.6 | 4.6 | |
| $C_{15}$ | 0.5 | 0.6 | 1.0 | 1.8 | 2.1 |
| $C_{16}$ | 1.5 | 46.7 | 48.5 | 34.2 | 0.6 |
| $C_{17}$ | — | 0.2 | 0.2 | 0.4 | 0.6 |
| $C_{18}$ | — | 8.0 | 28.5 | 56.1 | 95.8 |
| $C_{19}+$ | — | — | 0.2 | 0.4 | 0.9 |

The $C_{11}+$ fractions from runs VII–XI above were dimerized with n-propanol-boron trifluoride catalyst. The dimerization reactions were made in a glass flask as follows. To the flask that had been swept with nitrogen measured amounts of the olefin mixture plus light paraffinic hydrocarbon diluent and n-propanol were added. The flask stood in a water bath on a hot plate, was fitted with a high speed stirrer, and was vented through a mercury manostat that permitted operation at about five cm. mercury above atmospheric pressure. Boron trifluoride was added as required to maintain the reaction pressure. Reaction was initiated by warming gently to about 40° C., and was maintained at or near that temperature during the run. At the end of the run the catalyst was separated in a separatory funnel from the hydrocarbon phase, and the latter was washed with about 200 ml of an aqueous solution of a base, e.g., 1.3 normal sodium hydroxide or preferably 5 normal ammonium hydroxide, to remove dissolved boron trifluoride. The hydrocarbon was dried over activated 3 A molecular sieve, filtered, then distilled (in vacuum) to separate a <410° C. fraction and a lube oil (410°–510° C.) fraction. The lubricating oil fraction of the distillate was hydrogenated, after dilution with 100 ml of n-hexane, in an autoclave at 160° C. for two hours at $2.9 \times 10^6$ Pa hydrogen pressure over 0.25 g of 10% palladium on carbon catalyst. After hydrogenation the hexane diluent was removed by distillation and the resulting lubricating oil was inspected by standard methods for pertinent physical properties. Table III summarizes dimerization runs made with five different olefin mixtures and the properties of the products that were obtained.

TABLE III

| | Run | | | | |
|---|---|---|---|---|---|
| | XII | XIII | XIV | XV | XVI |
| Metathesis product from run | VII | VIII | IX | X | XI |
| Charge to dimerization reactor, g | | | | | |
| Olefin mixture | 107.6 | 77.6 | 78.3 | 78.7 | 121.0 |
| n-Hexane (diluent) | 110.6 | 138.8 | | | 102.0 |
| n-Heptane (diluent) | | | 136.7 | 135.4 | |
| n-Propanol | 2.3 | 2.4 | 3.2 | 3.2 | 2.3 |
| Boron trifluoride | ~2.7 | ~2.8 | ~3.7 | ~3.7 | ~2.7 |
| Dimerization conditions | | | | | |
| Time, hr. | 6 | 7 | 7 | 8 | 7 |
| Temp., °C. | 40 | 24–46 | 24–47 | 20–43 | 40 |
| Conversion of reactant olefins, wt. % | 80 | 74 | 77 | 70 | 76 |
| Selectivity to, wt. %: | | | | | |
| Lights (IBP ≦ 410° C.) | 7 | 5.5 | 5.4 | 2.5 | 2 |
| Lube oil (410–510° C.) | 81 | 84.8 | 82.3* | 80 | 77 |
| Heavies (>510° C.) | 12 | 9.7 | 12.3 | 17.5 | 21 |
| Properties of hydrogenated lube oil | | | | | |
| Viscosity, SUS at 100° F. | 101.7 | 101.7 | 125.0 | 116.4 | 133.2 |
| Viscosity, SUS at 210° F. | 39.7 | 40.6 | 42.3 | 41.7 | 43.6 |
| Viscosity Index | 105 | 115 | 120 | 124 | 134 |
| Pour point, °C. | <−54 | −54 | −48 | −37 | −34 |

*415–520° C.

EXAMPLE 2

Two dimerization runs were also made using an 85% phosphoric acid-boron trifluoride catalyst. One used an olefin feed having a composition resembling that from run IX in Table II. The other contained, in addition, heavier olefins from the <410° C. fraction that had been isolated by distillation from a previous run. Table IV summarizes the olefin feed composition, dimerization conditions and results, and pertinent physical properties of the lubricating oil. In these runs a preformed catalyst was used, i.e., boron trifluoride was not added through the reaction period.

TABLE IV

| | Run | |
|---|---|---|
| | XVII | XVIII |
| Composition of metathesis product used, wt. % | | |
| $C_{11}$ | 0.3 | 0.3 |
| $C_{12}$ | 0.4 | 0.3 |
| $C_{13}$ | 1.8 | 1.1 |
| $C_{14}$ | 21.4 | 11.6 |
| $C_{15}$ | 2.1 | 43.2 |
| $C_{16}$ | 48.1 | 43.2 |
| $C_{17}$ | 0.7 | 1.8 |
| $C_{18}$ | 25.2 | 32.1 |
| $C_{20-24}$ | | 6.9 |
| $C_{28}+$ | | 2.7 |
| Charge to dimerization reactor, g | | |
| n-Hexane (diluent) | 107 | 141 |
| Olefin mixture | 208.5 | 247.3 |
| 52.5 wt. % $BF_3$ in 85% $H_3PO_4$ | 118.0 | 107.2 |
| Dimerization conditions | | |
| Time, hr. | 6 | 8 |
| Temp., °C. | 30–43 | 30–60 |
| Conversion of reactant olefins, wt. % | 82.4 | 44 |
| Selectivity to, wt. % | | |
| Lights (IBP ≦ 410° C.) | 22.5 | 4.7 |
| Lube oil (410–510° C.) | 58.1 | 84.4 |
| Heavies (<510° C.) | 19.4 | 10.9 |
| Property of hydrogenated lube oil | | |
| Viscosity, SUS at 100° F. | 109.6 | 130.8 |
| Viscosity, SUS at 210° F. | 41.2 | 42.7 |
| Viscosity index | 125 | 121 |
| Pour Point, °C. | −37 | −32 |

*>520° C.

Properties of the lubricating oil obtained from using the phosphoric acid-boron trifluoride dimerization catalyst are very similar to those of the oil prepared from the n-propanol-boron trifluoride catalyst. However selectivity to lubricating oil from the phosphoric acid catalyst was lower than with the n-propanol catalyst.

These results from the use of phosphoric acid-boron trifluoride catalyst, which as for a long time been known to be active for olefin dimerization and polymerization show that the results when using an alcohol-boron trifluoride catalyst are unexpectedly superior to those using the phosphoric acid promoted boron trifluoride catalyst for making a lubricating oil.

EXAMPLE 3

7-Tetradecene was dimerized with aluminum chloride as follows: 83.0 g of 7-tetradecene to which 1.3 g fresh aluminum chloride and 0.1 g water had been added was heated in a magnetically stirred flask to about 50° C. Sample A was taken after one hour. After five hours, 4.0 g nitromethane and 0.7 g additional aluminum chloride were added to the flask. Sample B was taken after two additional hours of stirring. Table V summarizes the analytical information from these samples.

TABLE V

|  | SAMPLE | |
| --- | --- | --- |
|  | A | B |
| Time at 50° C., hours | 1 | 7 |
| Conversion of 7-$C_{14}H_{28}$, % | 7 | 10 |
| Selectivity to |  |  |
| $C_{20}$-$C_{22}$, % | 4 | 4 |
| $C_{24}$-$C_{40}$ | 89 | 70 |
| >$C_{40}$ | 7 | 26 |

Conversion of 7-tetradecene increased with time, but selectivity to lube oil ($C_{24}$-$C_{40}$) decreased. This example demonstrates that Friedel-Crafts catalysts can be used in the process of this invention; presently, $BF_3$ is the preferred catalyst, however.

Reasonable variations and modifications which will become apparent to those skilled in the art can be made from this invention without departing from the spirit and scope thereof.

We claim:

1. A process for producing a hydrocarbon oil comprising contacting an internal olefin having the formula

R—CH=CH—R'

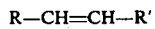

wherein R and R' which can be the same or different each represent an alkyl radical of 4-12 carbon atoms, under dimerization conditions with alcohol-promoted boron halide as a dimerization catalyst to produce a mixture comprising said hydrocarbon oil.

2. A process in accordance with claim 1 wherein
    (a) at least one alpha olefin having the formula

R"—CH=CH$_2$

wherein R" has the same meaning as R and R', is contacted under disproportionation conditions with a disproportionation catalyst to produce a first product comprising unreacted alpha olefins and said internal olefin,
    (b) said internal olefin and said unreacted alpha olefin are separated to form a second product comprising said internal olefin but being essentially free of unreacted alpha olefin,
    (c) said second product is contacted with said dimerization catalyst.

3. A process in accordance with claim 2 wherein said disproportionation catalyst is an oxide of rhenium catalyst.

4. A process in accordance with claim 2 wherein said alpha olefin is one having 8, 9 or 10 carbon atoms.

5. A process in accordance with claim 2 wherein step (b) is carried out by heating said first product in a heating zone to a temperature between the boiling point of said alpha olefin and the boiling point of said internal olefin to evaporate said unreacted alpha olefin and by withdrawing a stream containing alpha olefin vapors from said heating zone, both boiling points referring to that temperature at which the specified hydrocarbon boils at the operating pressure.

6. A process in accordance with claim 5 wherein at least a portion of said alpha olefin vapors is recycled to said disproportionation reaction in step (a).

7. A process in accordance with claim 1 comprising
    (a) removing said dimerization catalyst from said mixture to produce a hydrocarbon fluid,
    (b) subjecting said hydrocarbon fluid to a distillation to remove unreacted internal olefin from said hydrocarbon fluid leaving a hydrocarbon liquid,
    (c) subjecting said hydrocarbon liquid to a distillation at a temperature above the boiling point of the dimer of said internal olefin under the given pressure of the vacuum distillation to produce a purified hydrocarbon oil.

8. A process in accordance with claim 7 where said hydrocarbon oil prior to or after said vacuum distillation step (c) is contacted under hydrogenation conditions with molecular hydrogen and a hydrogenation catalyst such as to remove essentially all of the olefinic unsaturation from the hydrocarbon oil.

9. A process in accordance with claim 2 wherein ethylene formed during the reaction of step (a) is continuously removed from a reaction zone in which the disproportionation reaction of step (a) is carried out.

10. A process in accordance with claim 1 wherein said dimerization catalyst comprises alcohol-promoted boron trifluoride.

11. A process in accordance with claim 2 wherein said at least one alpha olefin is a normal alpha olefin.

* * * * *